(12) United States Patent
DeGuillebon

(10) Patent No.: US 6,595,984 B1
(45) Date of Patent: Jul. 22, 2003

(54) LAPAROSCOPIC INSTRUMENT WITH A DETACHABLE TIP

(75) Inventor: Henri F. DeGuillebon, Manchester-by-the-Sea, MA (US)

(73) Assignee: Microline, Inc., Beverly, MA (US)

( * ) Notice: Subject to any disclaimer, the term of this patent is extended or adjusted under 35 U.S.C. 154(b) by 0 days.

(21) Appl. No.: 09/536,553

(22) Filed: Mar. 28, 2000

(51) Int. Cl.$^7$ ................................................ A61B 17/00
(52) U.S. Cl. .......................................... 606/1; 600/136
(58) Field of Search .............................. 606/1; 600/136

(56) References Cited

U.S. PATENT DOCUMENTS

| | | | | |
|---|---|---|---|---|
| 3,574,374 A | * | 4/1971 | Keller et al. ................. 287/119 |
| 4,679,556 A | * | 7/1987 | Lubock et al. ............... 128/303 |
| 4,896,986 A | * | 1/1990 | Terayama ..................... 403/14 |
| 5,222,956 A | * | 6/1993 | Waldron ....................... 606/80 |
| 5,265,343 A | * | 11/1993 | Pascaloff ..................... 30/339 |
| 5,358,508 A | * | 10/1994 | Cobb .......................... 606/174 |
| 5,490,683 A | * | 2/1996 | Micket et al. ................ 279/75 |
| 5,578,052 A | * | 11/1996 | Koros et al. ................. 606/174 |
| 5,609,603 A | * | 3/1997 | Linden ........................ 606/177 |
| 5,741,084 A | * | 4/1998 | Del Rio et al. .............. 403/349 |
| 5,782,836 A | * | 7/1998 | Umber et al. ................. 606/79 |
| 5,810,879 A | * | 9/1998 | de Guillebon ............... 606/205 |
| 5,989,257 A | * | 11/1999 | Tidwell et al. ................ 606/79 |
| 6,113,586 A | * | 9/2000 | Ouchi ........................... 606/1 |
| 6,209,886 B1 | * | 4/2001 | Estes et al. .................. 279/50 |

* cited by examiner

*Primary Examiner*—Linda C. M. Dvorak
*Assistant Examiner*—Jocelyn Ram

(57) ABSTRACT

A laparoscopic assembly includes a body, an elongated shaft, and optionally, a removable or non-removable surgical tip. The body includes a casing manually manipulating tip actuating means, a tip actuating rod, a collet, a collet closer, and one or more collet detent members. The shaft is operably and removably gripped by the body and extends from the body to interconnect the body with a surgical tip. The collet closer is shaped and sized to, on tightening of the collet closet, radially compress the collet to grip the sheath. Each collet detent member is disposed in one collet radial bore, and is shaped and sized to permit only partial entry into the collet axial bored to engage the sheath depression during assembly, and be freely movable radially within the collet radial bore in response to urging inwardly by the tightening of the collet closer, or outwardly by the sheath depression wall when the collet closer is loosened.

12 Claims, 3 Drawing Sheets

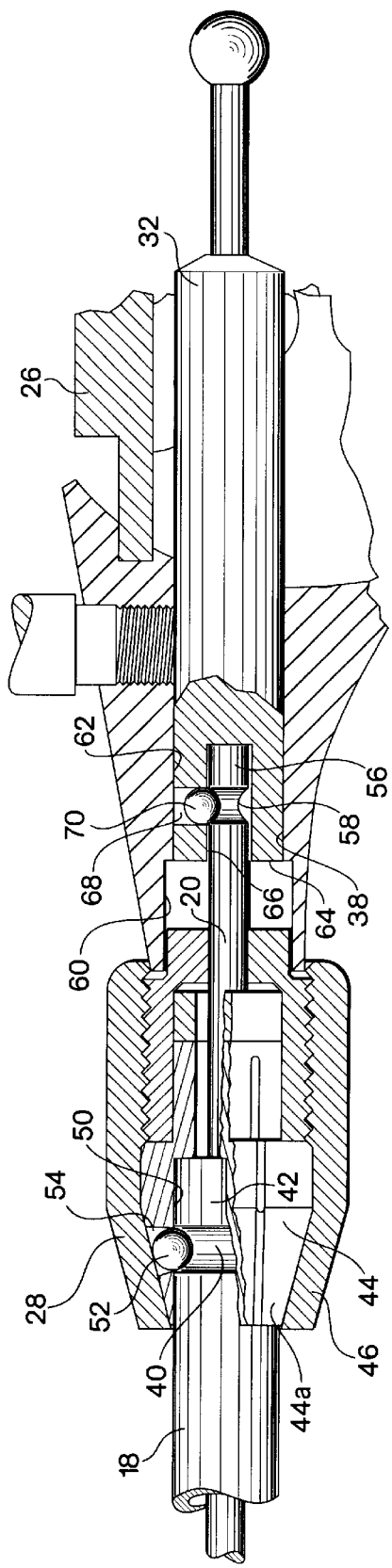
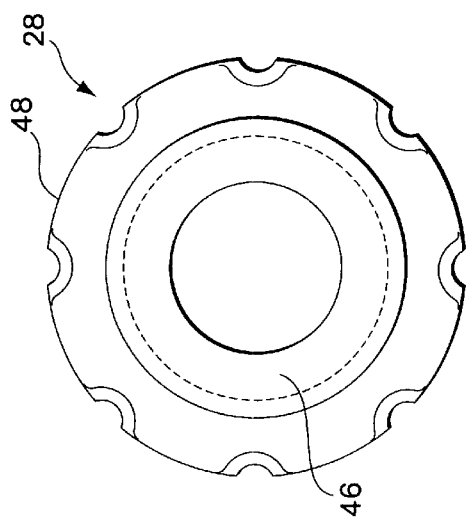
Fig. 4
Fig. 2
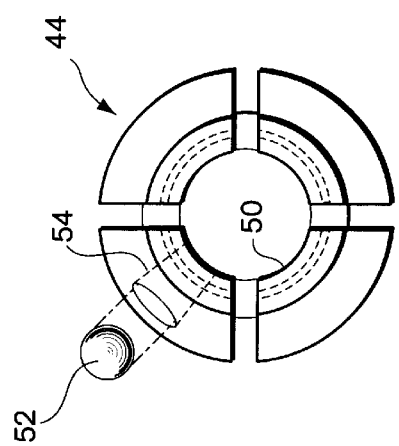
Fig. 3

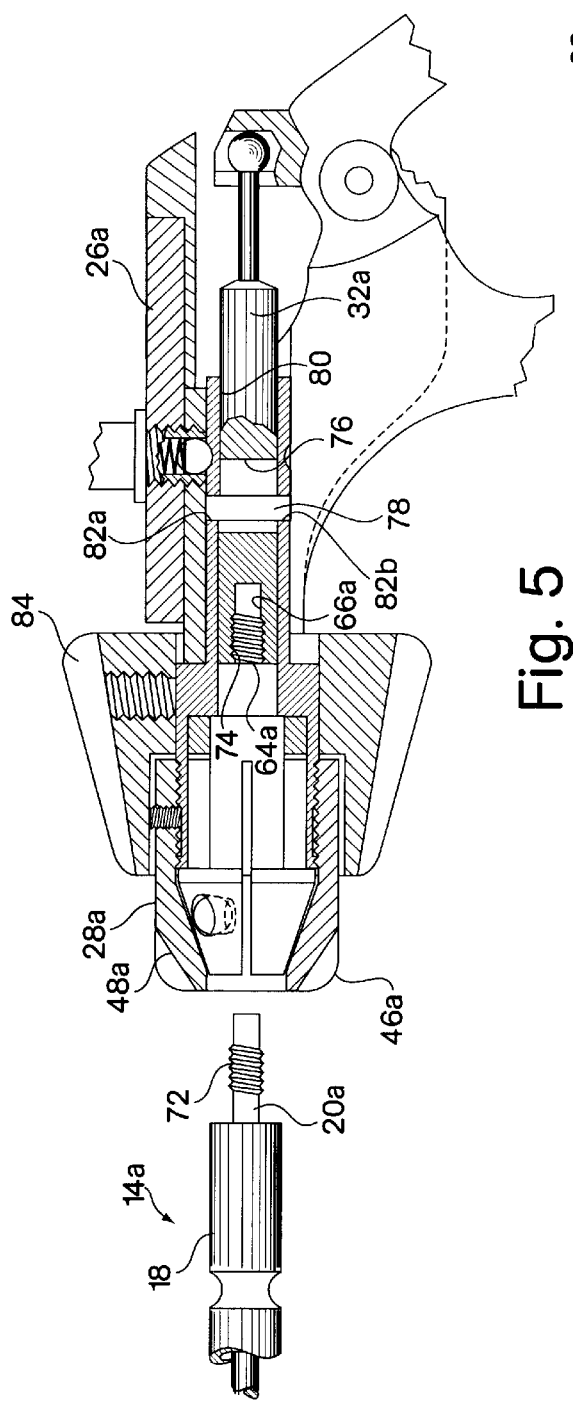
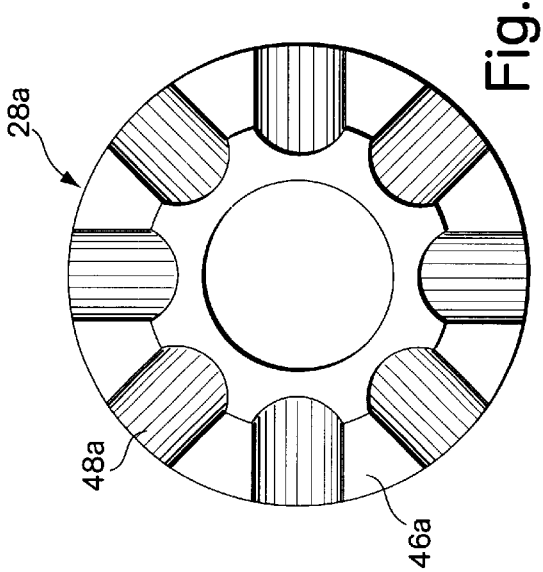
Fig. 7
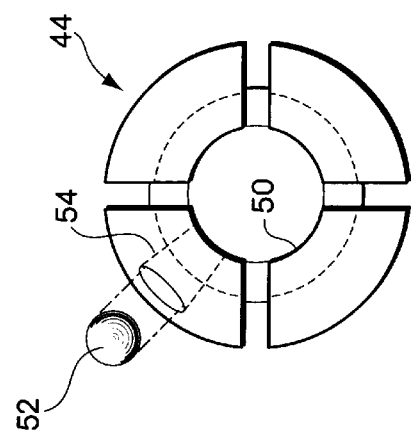
Fig. 6
Fig. 5

LAPAROSCOPIC INSTRUMENT WITH A DETACHABLE TIP

CROSS-REFERENCE TO RELATED APPLICATIONS

The present application contains subject matter related to U.S. Pat. Nos. 5,358,508 and 5,810,879, both commonly assigned herewith and incorporated herein by reference.

BACKGROUND OF THE INVENTION

The present invention relates to a laparoscopic instrument, and more particularly to a laparoscopic instrument having a manually operable tip, such as cutting blades, forceps, or the like, and to a removable shaft therefor.

A wide variety of medical instruments for laparoscopic surgery are presently known. Such instruments are used to access, e.g., the peritoneal cavity of a patient through a small incision in the abdominal wall. An endoscope normally is inserted into the cavity through a second incision in the abdominal wall for viewing of the operation of the instrument by the surgeon. Typical of such laparoscopic instruments are those having a tip end including, e.g., cutting blades, forceps, or other surgical device to be inserted into the cavity to perform the surgery; an external end from which the surgeon may manually manipulate the tip device from a position external to the abdominal wall; and an elongated shaft operably connecting the tip end and the external end. Many such laparoscopic instruments have permanently attached tips. However, in recent years instruments have been developed having disposable tips. Thus, a worn cutting blade may be replaced or one type of tip may be replaced with another, interchangeable type.

Because of the high cost of such laparoscopic instruments, reuse of each instrument, or part of each instrument, would be advantageous in controlling the cost of laparoscopic surgery. However, such reuse requires instruments of rugged construction which may be readily cleaned and sterilized. Known laparoscopic instruments, even those with removable tips, can be difficult to clean due to their length and complex internal structure.

Above-referenced Pat. No. 5,810,879 describes a laparoscopic instrument assembly in which the shaft and the body of the assembly may be readily disassembled. The shaft between the tip and the externally manipulable body of the instrument includes a rod moving axially within a sheath to transmit the manipulation of a tip actuating mechanism within the body to actuate the tip. The sheath is removable from the body for cleaning of the instrument, i.e., after use of the instrument, the shaft may be readily disassembled from the body, the shaft and body sterilized, and the shaft and body readily reassembled for reuse of the instrument. Alternatively, the shaft may be disposed of and the body reassembled with a fresh shaft. The assembly may be used with a removable tip provided separately, or a removable or non-removable tip may be provided as part of the assembly. In this type of instrument, the tubular sheath is secured within the body by compression applied by the action of a collet closer on a collet within the body. It would be desirable, however, to provide additional securing means for improved retention and stabilization of the sheath within the collet during operation of the instrument.

SUMMARY OF THE INVENTION

Accordingly, it is an object of the present invention to provide a laparoscopic instrument which overcomes the disadvantages of the prior art.

It is another object of the invention to provide a laparoscopic instrument assembly, including additional sheath securing means, which is easily and thoroughly cleaned by normal hospital equipment and procedures.

It is yet another object of the invention to provide a laparoscopic instrument assembly, including additional sheath securing means, in which the shaft and body of the instrument are readily disassembled for cleaning and reassembled for reuse.

It is yet another object of the invention to provide a shaft for a laparoscopic instrument, including means for securing the sheath within the body of the instrument.

In accordance with these objects, in one aspect the invention is a laparoscopic instrument assembly including a handle member or body, an elongated shaft operably and removably gripped by the body and extending from the body to interconnect the body with a surgical tip, and, optionally, a removable or non-removable surgical tip.

The body includes a casing, manually manipulable tip actuating means, and a tip actuating rod, and also includes a collet and a collet closer each coaxial with an axial bore through the casing. The body further includes one or more collet detent members, e.g., balls, to secure a sheath portion of the shaft within the body, as described below.

The shaft extends from the body to interconnect the body with a tip, and includes a tubular sheath and a rod having a body end and a tip end. The shaft rod is movable axially within the sheath in response to movement of the tip actuating rod by the tip actuating means to transmit manipulation of the tip actuating means to actuate the surgical tip. The sheath also has a body end and a tip end. An external surface of the sheath includes at the body end thereof at least one detent member-receiving depression, e.g., a groove to receive the collet detent members. One or both of the tip actuating rod and the shaft rod include means for operably and removably connecting the shaft rod to the tip actuating rod.

The collet includes an axial bore therethrough dimensioned for close sliding fit about the sheath and one or more radial bores extending radially through the collet from an outer surface thereof to be open to the axial bore. The collet radial bores are of a first, larger diameter at the collet outer surface and a second, smaller diameter at an opening of the collet radial bores into the collet axial bore.

The collet closer is shaped and sized to, on tightening of the collet closer, radially compress the collet to grip the sheath. Each collet detent member is disposed in one of the collet radial bores. Each collet detent member is shaped and sized to (a) permit only partial entry of the collet detent member into the collet axial bore to engage the sheath depression during assembly of the instrument assembly, and (b) be freely movable radially within its collet radial bore in response to urging inwardly by an internal surface of the collet closer as it is tightened during assembling of the instrument assembly, or outwardly by a wall of the sheath depression when the collet closer is loosened during disassembling of the instrument assembly.

In a narrower embodiment, the laparoscopic instrument assembly further includes the surgical tip, which may be removable or non-removable from the shaft. In another narrower embodiment, the collet and collet closer are each coaxial with the casing axial bore.

In another aspect, the invention is a body for a laparoscopic instrument including a body and an elongated shaft gripped by the body and extending from the body to interconnect the body with a surgical tip. The body includes a casing, manually manipulable tip actuating means, a tip actuating rod including means for operably and removably connecting a shaft rod of the shaft to the tip actuating rod.

The body further includes a collet, a collet closer, and one or more collet detent means. The collet includes an axial bore therethrough dimensioned for close sliding fit about a sheath of the shaft and one or more radial bores extending radially through the collet from an outer surface thereof to be open to the axial bore. The collet radial bores are of a first, larger diameter at the collet outer surface and a second, smaller diameter at an opening of the collet radial bores into the collet axial bore. The collet closer is shaped and sized to, on tightening of the collet closer, radially compress the collet to grip the sheath. The one or more collet detent members are each disposed in one of the collet radial bores. Each collet detent member is shaped and sized to (a) permit only partial entry of the collet detent member into the collet axial bore to engage a depression on the shaft sheath during-assembly of the instrument assembly, and (b) be freely movable radially within its collet radial bore in response to urging inwardly by an internal surface of the collet closer as it is tightened during assembling of the instrument assembly, or outwardly by a wall of the sheath depression when the collet closer is loosened during disassembling of the instrument assembly.

In yet another aspect, the invention is an elongated shaft for a laparoscopic instrument including a body having a tip actuating rod, the shaft being gripped within the instrument by the body to extend from the body to interconnect the body with a surgical tip. The shaft includes a tubular sheath having a body end and a tip end. An external surface of the sheath includes at the body end thereof at least one detent member-receiving depression, e.g., a groove. The shaft further includes a rod axially moveable within the sheath. The shaft rod has a body end and a tip end, and includes means at the rod body end for operably and removably connecting the shaft rod to the tip actuating rod. In a narrower embodiment, the shaft further includes the surgical tip, the surgical tip being removable or non-removable from the shaft.

BRIEF DESCRIPTION OF THE DRAWINGS

For a better understanding of the present invention, together with other objects, features, advantages, and capabilities thereof, reference is made to the following Description and appended Claims, together with the Drawings in which:

FIG. 2 is an elevation view, partly in section, of portions of the shaft and body of the assembly of FIG. 1, showing the sheath detent mechanism in further detail;

FIG. 3 is an exploded elevation view of the collet of FIGS. 1 and 2, showing the detent member and radial bore;

FIG. 4 is an elevation view of the collet closer of FIGS. 1 and 2;

FIG. 5 is an elevation view, partly in section, of the portions of the shaft and body of a laparoscopic instrument assembly in accordance with another embodiment of the invention;

FIG. 6 is an exploded elevation view of the collet of FIG. 5, showing the detent member and radial bore;

FIG. 7 is an elevation view of the collet closer of FIG. 5.

DETAILED DESCRIPTION OF THE PREFERRED EMBODIMENTS

Figure 1:
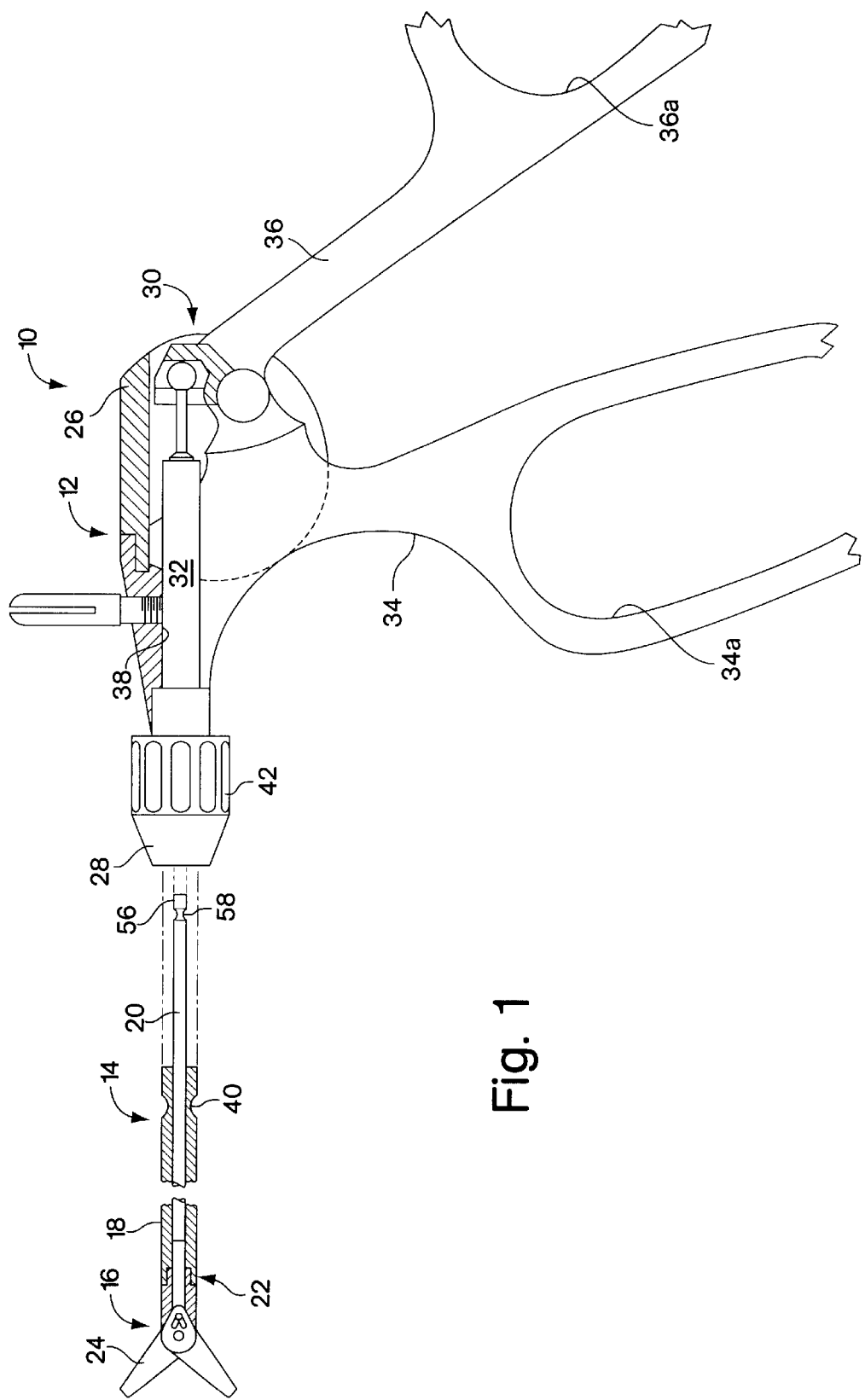
FIG. 1 is an exploded elevation view, partly in section, of a laparoscopic instrument assembly in accordance with one embodiment of the present invention.

The laparoscopic instrument assembly described herein includes a body and a shaft operably interconnecting the body to a surgical tip. The shaft includes a tubular sheath and a rod movable within the sheath. One end of the shaft may be operably connected to the tip for actuation of a surgical device on the tip. The instrument assembly may be used with a separately provided surgical tip or, optionally, the assembly may include a removable or non-removable tip. The other end of the shaft is removably and operably connected to the body and the shaft rod is movable axially within the sheath for transmission to the tip surgical device of handle member manipulation by the operator.

The body includes a casing, manually manipulable tip control means, a collet, a collet closer, and at least one collet detent member. The sheath is removably secured within the body by the compressive action of the collet closer on the collet and collet detent member. After use, the shaft may be readily disassembled from the body and, if desired, the shaft and body may be sterilized and readily reassembled for reuse of the instrument. Alternatively, the shaft may be disposed of and the body reassembled with a fresh shaft.

To assemble the instrument, the rod and sheath of the shaft are inserted into the collet axial bore, and the rod is secured within the instrument body for movement within the sheath in response to manipulation of the tip actuating means of the body. The collet closer is tightened, forcing the collet detent member inward to engage the groove or depression in the sheath. The securing of both the rod and the sheath within the body prevents removal of the shaft from the body during use of the instrument. For disassembly of the instrument, the collet closer is loosened, permitting disengagement of the detent member from the sheath groove or depression and, upon disengagement of the rod from the body, permitting removal of the shaft from the body.

On attachment of the tip to the shaft distal end, if required, actuation of the surgical device is effected by movement of the tip control means within an axial bore through the body, and movement of the shaft rod within the sheath in response to the movement of the tip control means.

The means for operably and removably attaching the tip control means typically includes a rod which moves within the bore through the body in response to manipulation of a handle as described below. In one embodiment, this tip control rod is attached to the shaft rod by threads on the body end of the shaft rod which engage a threaded axial bore in one end of the tip control rod. In another embodiment, the tip control rod also includes an axial bore into its shaft end and at least one detent member, e.g., a ball, disposed in a radial bore through the tip control rod. This additional detent member is engageable with, e.g., a groove on the body end of the shaft rod, holding the shaft rod to the tip control rod.

The description below of various embodiments shown in the Drawings refers to laparoscopic instruments in accordance with the invention. However, this description is not intended to limit the scope of the present invention, but merely to be illustrative and representative thereof.

Referring now to FIG. 1, laparoscopic instrument assembly 10 in accordance with one embodiment of the present invention includes body 12 and shaft 14 operably interconnecting body 12 and removable tip 16. Removable tip 16 may be provided as part of assembly 10 or, alternatively, may be obtained separately. Shaft 14 includes tubular sheath 18 and rod 20 movable within sheath 18. Tip end 22 of shaft 14 is operably connected to tip 16 for actuation of surgical device 24 on tip 16. Body 12 includes, inter alia, casing 26, collet closer 28, tip actuating means 30, and tip actuating rod 32. Tip actuating means 30 includes stationary handle 34 and finger-operable, movable handle 36 pivotally linked to stationary handle 34. Tip actuating rod 32 is linked to moveable handle 36 for sliding axial movement within axial bore 38 through casing 26 in response to pivotal movement of movable handle 36. Conveniently, stationary handle 34 and movable handle 36 include openings 34a and 36a shaped to receive fingers and thumb, respectively, of the operator for scissors-like manipulation of the instrument.

As shown in FIG. 2, sheath 18 includes groove 40 at body end 42 and, when held within casing 26, is coaxial with bore 38 of the casing. Sheath 18 is held in conventional manner within casing 26 using collet 44, shown in further detail in FIG. 3, and collet closer 28, shown in further detail in FIG. 4. Collet closer 28 includes conical portion 46 and ring portion 48. Collet 44 includes conical portion 44a and collet axial bore 50, coaxial with axial bore 38 through casing 26.

Additional sheath securing means are provided to ensure that sheath 18 is tightly secured within the body. Conical portion 44a of collet 44 includes at least one radial bore 54 within each of which a collet detent member 52 moves. Each collet radial bore 54 is of a larger diameter at its outer end where it is open to an internal surface of collet closer conical portion 46, and is of a smaller diameter at its inner end where it is open to collet axial bore 50. When collet closer 28 is tightened about collet 44 by turning ring portion 48, detent member 52 is forced inwardly by the internal surface of collet closer conical portion 46, partially enters collet axial bore 50, and engages sheath groove 40 to hold sheath 18 firmly within body 12. Detent member 52 is held in groove 40 by the close fit of the collet closer conical portion about the collet. on loosening of collet closer 28 and collet 44, pulling of sheath 18 away from body 12 moves a wall of sheath groove 40 against detent member 52, moving the detent member outwardly within collet radial groove 54 and releasing sheath 18 from body 12. Each collet detent member 52 is shown in the Figures as a ball. However, detent members 52 may be any shape and size which will (a) permit only partial entry of each collet detent member 52 into collet axial bore 50 to engage groove 40; and (b) to be freely movable radially within its radial bore 54 in response to urging inwardly from the internal surface of conical portion 46 or to urging outwardly by a wall of groove 40. The number of detent members 52 and bores 54 is selected to optimize the gripping power of the detent members on sheath 18.

Rod 20 is operably and removably connected to tip actuating rod 32 for axial movement of rod 20 within sheath 18 in response to movement of rod 32 within bore 38. Above-referenced U.S. Pat. No. 5,810,879 describes two embodiments of an instrument assembly with such connection.

FIG. 2 shows one embodiment in which body end 56 of shaft rod 20 removably and operably connected to tip actuating rod 32 of body 12 for transmission to the tip surgical device of manipulation by the operator of tip actuating means 30. Shaft rod 20 includes groove 58 at its body end 56. Casing axial bore 38 includes larger diameter portion 60 at the end of the bore near collet 44 and smaller diameter portion 62 nearer tip actuating means 30. The diameter of narrower portion 62 is selected for close sliding fit of tip actuating rod 32 therein. End 64 of rod 32 includes axial bore 66 extending inwardly from end 64 and sized for close sliding fit of rod 20 therein. At least one radial bore 68 is also formed in rod 32 to extend from the outer surface of rod 32 into and open to axial bore 66. The position of radial bore 68 is selected for registry of radial bore 68 with shaft rod groove 58. Each radial bore 68 has a larger diameter at the rod outer surface and a smaller diameter where it enters axial bore 66.

Each radial bore 68 contains a detent member 70 therein for mating engagement of detent member 70 with groove 58. The number of detent members 70 is selected to optimize the gripping power of the detent members on rod 20. Typically, from one to six detent members and radial bores are provided, with three the preferred number. Each detent member 70 is shown in the Figures as a ball. However, detent members 70 may be any shape and size which will (a) permit only partial entry of each detent member 70 into axial bore 66; (b) to be freely movable radially within its radial bore 68 in response to urging from the wall of narrow portion 62 of axial bore 32 or from a wall of groove 58; and (c) to extend beyond its radial bore 68 either into axial bore 66 to engage groove 58 or into wider portion 60 of the casing axial bore, but not into both.

Each detent member 70 engages groove 58 during actuation of tip surgical device 24, preventing removal of rod 20 from axial bore 66. However, sheath 18 may be released from casing 26 as described above, and detent members 70 may be disengaged from groove 58 by separating handle members 34 and 36 (FIG. 1) sufficiently wide apart to drive rod 32 distally beyond its operating position, bringing radial bores 68 and detent members 70 in registry with larger portion 60 of the casing axial bore. In this position, pulling of shaft 14 forces the side wall of groove 58 against detent members 70, forcing the detent members out of groove 58 and into larger portion 60 of the casing axial bore, permitting removal of shaft rod 20 from tip actuating rod 32 and separation of shaft 14 from body 12.

For reassembly, e.g., after cleaning, the steps are reversed. With tip actuating rod 32 in position nearest the collet, shaft 14 is inserted into body 12 with sheath 18 in position within collet axial bore 50 and rod 20 inserted into axial bore 66 of tip actuating rod 32 with groove 58 in registry with radial bores 68. Handles 34 and 36 then may be brought closer together, drawing rod 32 closer to the handles. Narrower portion 62 of the casing axial bore then forces detent members 70 out of larger portion 60 of the casing axial and into groove 58, locking rod 20 to rod 32. Detent members are held in groove 50 by the close sliding fit of rod 32 within narrower portion 48 of axial bore 34. Collet closer 28 is used as described above to tighten collet 38 against sheath 18 and to force detent member 52 into groove 40.

For use, removable tip 16 is attached to distal end 22 of shaft 18 in known manner, and surgical device 24, e.g., cutting means or forceps, is actuated by scissor-like movement of handles 34 and 36, which effects axial movement of rod 32 within the casing axial bore. Axial movement of rod 32 effects axial movement of rod 20 within and relative to sheath 18, which actuates surgical device 24 of tip 16 in known manner. In various embodiments, shaft 14 may be provided without a tip, or a removable or non-removable tip may be provided as part of the shaft.

FIG. 5 shows an alternate embodiment if the laparoscopic instrument assembly. Like features to those shown in FIGS. 1–4 are indicated by the same reference numerals. FIG. 5 shows in detail an alternate detent mechanism for operably and removably attaching the shaft rod to the tip actuating rod. Sheath 18 of shaft 14a is attached to casing 26a as described above. Body end 56a of rod 20a includes external threads 72 for mating engagement with internal threads 74 in axial bore 66a in rod 32a. Thus, body end 56aof rod 20a may be attached to end 64a of rod 32a by screwing threads 72 into threads 74.

To permit rotation of rod 20a relative to rod 32a for separation of rods 20a and 32a, while permitting axial movement of rod 32a, rod 32a is provided with slot 76. Pin 78 extends through slot 76 and is held in place within casing 26a in conventional manner. For example, casing 26a may include casing sheath 80 with opposing radial bores 82a and 82b to receive and hold in place pin 78. The relative sizes of slot 76 and pin 78 are selected to permit free axial movement of rod 32a within a range sufficient to manipulate a tip surgical device attached to shaft 14a. Rotational movement of rod 32a within the casing, however, is prevented by pin 78.

FIGS. 6 and 7 show collet 44 and collet closer 28a of FIG. 5, which are particularly suited to a smaller instrument than is shown in FIG. 1. The instrument design shown in FIG. 1 is preferred for instruments having a shaft diameter of 1–4 mm, while the design shown in FIG. 5 is preferred for those having a shaft diameter of 3–10 mm. Collet 44 of FIG. 6 is of the same design as collet 44 of FIG. 3. However, conical portion 46a of collet closer 28a includes grooved surface 48a. Grooved surface 48a serves the same purpose as ring 48 of collet closer 28 of FIG. 4, that is turning the collet closer for assembly and disassembly of the instrument. This design of the collet closer allows for the addition of grooved grip ring 84 to body 12, providing a firmer grip for the operator to hold and manipulate the smaller instrument.

The invention described herein presents to the art a novel, improved laparoscopic instrument assembly having a removable and replaceable or disposable shaft, with or without a tip. The assembly is simply and economically fabricated and the sheath portion of the shaft is readily and more securely held within the body of the assembly during operation of the instrument.

While there has been shown and described what are at present considered the preferred embodiments of the invention, it will be apparent to those skilled in the art that =modifications and changes can be made therein without departing from the scope of the present invention as defined by the appended Claims.

I claim:

1. A laparoscopic instrument assembly comprising
    a body including a casing having an axial bore, manually manipulable tip actuating means, a tip actuating rod, a collet, a collet closer, and one or more collet detent members; and
    an elongated shaft operably and removably gripped by said body and extending from said body to interconnect said body with a surgical tip, said shaft including a tubular sheath and a shaft rod, each having a body end and a tip end, said shaft rod being movable axially within said sheath in response to movement of said tip actuating rod by said tip actuating means to transmit manipulation of said tip actuating-means to actuate said tip;
    wherein an external surface of said sheath includes at said body end thereof at least one detent member-receiving depression;
    wherein at least one of said tip actuating rod and said shaft rod include means for operably and removably connecting said shaft rod to said tip actuating rod;
    wherein said collet includes an axial bore therethrough dimensioned for close sliding fit about said sheath and one or more radial bores extending radially through said collet from an outer surface thereof to be open to said axial bore; said collet radial bores are of a first, larger diameter at said collet outer surface and a second, smaller diameter at an opening of said collet radial bores into said collet axial bore;
    wherein said collet closer is shaped and sized to, on tightening of said collet closer, radially compress said collet to grip said sheath; and
    wherein each of said collet detent members is disposed in one of said collet radial bores, is shaped and sized to (a) permit only partial entry of said collet detent member into said collet axial bore to engage said at least one detent member-receiving sheath depression during assembly of said instrument assembly and (b) be freely movable radially within said collet radial bore in response to urging inwardly by an internal surface of said collet closer as it is tightened during assembling of said instrument assembly or outwardly by a wall of said at least one sheath depression when said collet closer is loosened during disassembling of said instrument assembly.

2. A laparoscopic instrument assembly in accordance with claim 1 further comprising said surgical tip, said surgical tip being removable or non-removable from said shaft.

3. A laparoscopic instrument assembly in accordance with claim 1 wherein said collet and said collet closer are each coaxial with said axial bore of said casing.

4. A laparoscopic instrument assembly in accordance with claim 1 wherein said at least one detent member-receiving, sheath depression is an annular groove about said shaft.

5. A laparoscopic instrument assembly in accordance with claim 1 wherein each of said one or more detent members is a ball.

6. A laparoscopic instrument assembly in accordance with claim 1 wherein said tip actuating rod has a shaft end and an actuating means end, and said means for operably and removably connecting said shaft rod to said tip actuating rod comprises:
    threads on one of said shaft rod body end and said shaft end of said tip actuating means rod, and a threaded axial bore in the other of said shaft rod body end and said tip actuating rod shaft end for mating engagement with one another to operably and removably connect said shaft rod to said tip actuating rod; and
    a pin fitting within a slot in said tip actuating rod to prevent rotational movement of said tip actuating rod relative to said casing, to permit free axial movement of said tip actuating rod within a range sufficient to actuate said tip, and to permit removal of said shaft rod from said tip actuating rod.

7. A laparoscopic instrument assembly in accordance with claim 1 wherein:
    said tip actuating rod has a shaft end and an actuating means end;
    said shaft rod includes an annular groove formed in said body end thereof;
    said tip actuating rod shaft end includes an inwardly extending rod axial bore shaped and sized for close sliding fit of said shaft rod therein;
    said tip actuating rod shaft end further includes one or more radial bores extending from an outer surface thereof to be open to said rod axial bore, each of said actuating rod radial bores being of a first, larger diameter at said actuating rod outer surface and a second, smaller diameter at said rod axial bore;
    said casing axial bore has a first, larger diameter portion adjacent said collet and a second, smaller diameter portion about said tip actuating means end of said tip actuating rod, the diameter of said second portion being selected for close sliding fit of said tip actuating rod therewithin; and said means for operably and removably connecting said shaft rod to said tip actuating rod further comprises a rod detent member disposed in each actuating rod radial bore and engageable with said shaft rod annular groove;

each of said rod detent members is shaped and sized to (a) permit only partial entry of said rod detent member into said actuating rod axial bore, (b) be freely movable radially within its associated actuating rod radial bore in response to urging from a wall of said casing axial bore second portion or from a wall of said shaft rod annular groove, and (c) extend beyond its associated actuating rod radial bore either into said rod axial bore to engage said shaft rod annular groove or into said casing axial bore first portion but not into both, preventing removal of said shaft rod from said tip actuating rod when said one or more actuating rod radial bores are adjacent said casing axial bore second portion and permitting removal of said shaft rod from said tip actuating rod when said one or more rod radial bores are adjacent said casing axial bore first portion.

8. A laparoscopic instrument assembly in accordance with claim 7 wherein said one or more actuating rod radial bores comprise 3–6 radial bores annularly arrayed about the circumference of said tip actuating rod distal end, each of said actuating rod radial bores containing one of said rod detent members engageable with said shaft rod annular groove.

9. A laparoscopic instrument assembly in accordance with claim 8 wherein each of said rod detent members is a ball.

10. A body for a laparoscopic instrument comprising a body and an elongated shaft gripped by said body and extending from said body to interconnect said body with a surgical tip, said body comprising:

a casing;

manually manipulable tip actuating means;

a tip actuating rod including means for operably and removably connecting a shaft rod of said shaft to said tip actuating rod;

a collet including an axial bore therethrough dimensioned for close sliding fit about a sheath of said shaft and one or more radial bores extending radially through said collet from an outer surface thereof to be open to said axial bore, wherein said collet radial bores are of a first, larger diameter at said collet outer surface and a second, smaller diameter at an opening of said collet radial bores into said collet axial bore;

a collet closer shaped and sized to, on tightening of said collet closer, radially compress said collet to grip said sheath; and one or more collet detent members each disposed in one of said collet radial bores, and shaped and sized to (a) permit only partial entry of said collet detent member into said collet axial bore to engage said depression on said sheath on said shaft during assembly of said instrument assembly, and (b) be freely movable radially within said collet radial bore in response to urging inwardly by an internal surface of said collet closer as it is tightened during assembling of said instrument assembly, or outwardly by a wall of said sheath depression when said collet closer is loosened during disassembling of said instrument assembly.

11. A laparoscopic instrument assembly in accordance with claim 10 wherein said collet and said collet closer are each coaxial with said axial bore in said casing.

12. A laparoscopic instrument assembly in accordance with claim 10 wherein each of said one or more detent members is a ball.

* * * * *